(12) United States Patent
Sosalla (10) Patent No.: US 7,384,386 B2
(45) Date of Patent: Jun. 10, 2008

(54) METHOD AND APPARATUS FOR FOLDING ARTICLES

(75) Inventor: Gerald Keith Sosalla, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 3 days.

(21) Appl. No.: 11/292,930

(22) Filed: Dec. 1, 2005

(65) Prior Publication Data

US 2007/0129230 A1    Jun. 7, 2007

(51) Int. Cl.
*B31F 1/30* (2006.01)
*B31F 7/00* (2006.01)

(52) U.S. Cl. ...................................... 493/441
(58) Field of Classification Search .............. 493/441, 493/417, 450
See application file for complete search history.

(56) References Cited

U.S. PATENT DOCUMENTS

| | | | |
|---|---|---|---|
| 2,848,220 A | | 8/1958 | Anderson |
| 3,572,689 A | | 3/1971 | Murphy et al. |
| 3,661,680 A | | 5/1972 | Gore |
| 3,998,447 A | | 12/1976 | Joa |
| 4,018,432 A | | 4/1977 | Frick |
| 4,022,456 A | | 5/1977 | Hooper et al. |
| 4,059,258 A | | 11/1977 | Grantham |
| 4,111,733 A | * | 9/1978 | Periers ................ 156/204 |
| 4,307,800 A | | 12/1981 | Joa |
| 4,508,528 A | | 4/1985 | Hirsch et al. |
| 4,650,173 A | | 3/1987 | Johnson et al. |
| 4,682,977 A | | 7/1987 | Buxton |
| 4,701,156 A | | 10/1987 | Larsonneur |
| 4,708,332 A | * | 11/1987 | Besemann ............... 270/39.05 |
| 5,176,615 A | | 1/1993 | Munsch |
| 5,360,387 A | * | 11/1994 | Baker ........................ 493/405 |
| 5,373,681 A | * | 12/1994 | Shigeta ....................... 53/225 |
| 5,537,802 A | * | 7/1996 | Orndorff ....................... 53/450 |
| 5,556,360 A | * | 9/1996 | Kober et al. .................. 493/23 |

(Continued)

FOREIGN PATENT DOCUMENTS

EP    0 475 202 B1    6/1995

(Continued)

OTHER PUBLICATIONS

Patent Cooperation Treaty Search Report from the International Search Authority, International Application No. PCT/US 2006/038934 dated Feb. 2, 2007.

*Primary Examiner*—Rinaldi Rada
*Assistant Examiner*—John Paradiso
(74) *Attorney, Agent, or Firm*—David J. Arteman (57) ABSTRACT

A method and apparatus for folding an article includes supplying an article to a folder; engaging a first surface of a leading portion of the article with a first conveyor; moving the first conveyor at a first conveyor velocity; engaging a second surface of a trailing portion of the article with a second conveyor; moving the second conveyor at a second conveyor velocity greater than the first conveyor velocity; contacting the first surface of the article with at least one folding guide; moving the folding guide in the machine direction at the second conveyor velocity; and folding the article about the folding guide such that the first surface of the leading portion is in facing relation with the first surface of the trailing portion.

10 Claims, 6 Drawing Sheets

U.S. PATENT DOCUMENTS

| | | |
|---|---|---|
| 5,743,994 A | 4/1998 | Roessler et al. |
| 5,788,805 A | 8/1998 | Herrmann |
| 5,797,831 A * | 8/1998 | Roberts et al. ............. 493/438 |
| 5,853,402 A | 12/1998 | Faulks et al. |
| 5,997,459 A * | 12/1999 | Kruger et al. .............. 493/441 |
| 6,015,934 A * | 1/2000 | Lee et al. .................... 604/358 |
| 6,065,521 A | 5/2000 | Tharpe, Jr. et al. |
| 6,315,022 B1 | 11/2001 | Herrin et al. |
| 6,551,431 B2 | 4/2003 | Lee |
| 6,723,035 B2 * | 4/2004 | Franklin et al. ............ 493/450 |
| 6,766,628 B2 * | 7/2004 | Guidetti ....................... 53/443 |
| 2003/0062113 A1 | 4/2003 | Van Eperen et al. |

FOREIGN PATENT DOCUMENTS

| | | |
|---|---|---|
| EP | 1 438 945 A1 | 7/2004 |
| FR | 2 456 694 A1 | 12/1980 |
| JP | 08-133589 A | 5/1996 |
| JP | 09-048405 A | 2/1997 |
| JP | 09-131364 A | 5/1997 |
| JP | 09-221268 A | 8/1997 |
| JP | 10-129926 A | 5/1998 |
| JP | 2004-141627 A | 5/2004 |

* cited by examiner

METHOD AND APPARATUS FOR FOLDING ARTICLES

BACKGROUND OF THE INVENTION

This invention relates to a method and apparatus for folding articles, such as, for example, disposable diapers. Typical folding systems move a leading portion of an article past a nip defined by two belts or rollers. After the leading portion of the article moves past the nip a tucker blade or similar apparatus orthogonally contacts the article creating a fold while forcing the folded article into the nip. This tucking and folding method involves a sudden and severe reversal in direction of the leading portion of the article which can result in folding inaccuracies and/or damage to the article particularly at high speeds.

As such, there exists a need for a method and apparatus for folding articles that is gradual and smooth thereby increasing the accuracy of the fold and minimizing damage to the article being folded.

SUMMARY OF THE INVENTION

In response to these needs, the present invention provides a method and apparatus for folding an article. In one aspect, the method includes supplying an article having a first surface and a second surface opposite the first surface, a leading portion, a trailing portion and a central portion connecting the leading portion and the trailing portion. The method also includes engaging the first surface of the leading portion of the article with a first conveyor; moving the first conveyor in a machine direction at a first conveyor velocity; engaging the second surface of the trailing portion of the article with a second conveyor; moving the second conveyor in the machine direction at a second conveyor velocity, the second conveyor velocity being greater than the first conveyor velocity; contacting the first surface of the article with at least one folding guide; moving the at least one folding guide in the machine direction at the second conveyor velocity; and folding the article about the at least one folding guide such that the first surface of the leading portion is in facing relation with the first surface of the trailing portion.

In various embodiments, the method may also include moving the first conveyor at the first conveyor velocity and moving the second conveyor at the second conveyor velocity wherein the ratio of the first conveyor velocity to the second conveyor velocity is less than 0.8 to 1.

In various embodiments, the method may also include peeling the first surface of the leading portion of the article from the first conveyor as the article moves between the first conveyor and the second conveyor.

In various embodiments, the method may also include applying vacuum to vacuum areas in the first conveyor and vacuum areas in the second conveyor and engaging the first surface of the leading portion of the articles with the vacuum areas of the first conveyor and engaging the second surface of the trailing portion of the articles with the vacuum areas of the second conveyor.

In various embodiments, the method may include lifting the leading portion of the article towards the vacuum areas of the first conveyor. In various embodiments, the method may further include lifting the leading portion of the article towards the vacuum areas of the first conveyor with profiles attached to the second conveyor.

In another aspect, a method for folding a diaper includes supplying a diaper to a folder. The diaper has a body side, a garment side opposite the body side, a leading portion, a trailing portion and a central portion connecting the leading portion and the trailing portion. The method includes engaging the garment side of the trailing portion of the diaper, via vacuum, to a perforated portion of a second conveyor; moving the second conveyor in the machine direction at a second conveyor velocity; lifting the leading portion of the diaper towards a perforated portion of a first conveyor; engaging the body side of the leading portion, via vacuum, to the perforated portion of the first conveyor; moving the first conveyor in the machine direction at a first conveyor velocity, the first conveyor velocity being less than the second conveyor velocity; contacting the body side of the diaper with a pair of folding guides; moving the folding guides in the machine direction at the second conveyor velocity; moving the diaper through a folding zone defined by the first conveyor and the second conveyor; peeling the body side of the leading portion of the diaper from the first conveyor as the diaper moves through the folding zone thereby folding the diaper about the pair of folding guides such that the body side of the leading portion is in facing relation with the body side of the trailing portion.

In various embodiments, the method further includes lifting the leading portion of the diaper towards the perforated portion of the first conveyor with profiles attached to the second conveyor.

In various embodiments, the method further includes folding the diaper so as to align a leading edge of the leading portion with a trailing edge of the trailing portion.

In various embodiments, the method further includes moving the first and second conveyors such that the ratio of the first conveyor velocity to the second conveyor velocity is less than 0.8 to 1.

The present invention also provides an apparatus that includes a first conveyor, a second conveyor and at least one folding guide. The first conveyor is adapted to move at a first conveyor velocity in a machine direction. The second conveyor is adapted to move at a second conveyor velocity in the machine direction and is positioned in facing relation with the first conveyor to define a folding zone therebetween. The second conveyor velocity is greater than the first conveyor velocity. The at least one folding guide is adapted to move at the second conveyor velocity in the machine direction through the folding zone in contact with an article being folded therein.

In various embodiments, the apparatus further includes a plurality of folding guide pairs adapted to move into the folding zone at a folding zone entrance and move out of the folding zone at a folding zone exit.

In various embodiments, the folding zone includes longitudinal sides and the folding guides are attached to two guide transporters located along each longitudinal side. The guide transporters are adapted to move the folding guides only in the plane defined by the machine direction and a cross-machine direction. In various embodiments, the guide transporters are timing belts moving about shafts aligned perpendicular to the plane defined by the machine direction and the cross-machine direction.

In various embodiments, the folding zone includes longitudinal sides. The folding guides are attached to two guide transporters located along each longitudinal side and the guide transporters are adapted to move the folding guides in a plane defined by the machine direction and a cross-machine direction in the folding zone and in a plane perpendicular to the plane defined by the machine direction and the cross-machine direction outside the folding zone. In various embodiments, the guide transporters include cam tracks and the folding guides include cam followers.

In various embodiments, the first conveyor and the second conveyor may include vacuum permeable zones and vacuum impermeable zones. In various embodiments, the second conveyor may further include profiles between the vacuum permeable zones. The profiles may be adapted to lift the product being folded into closer proximity to the first conveyor.

In various embodiments, the ratio of the first conveyor velocity and the second conveyor velocity may be adapted to be less than 0.8 to 1.0.

DETAILED DESCRIPTION OF THE DRAWINGS

The method and apparatus of the present invention will be described herein with reference to folding an absorbent article, such as, for example an infant diaper. The method and apparatus are also suitable for folding other absorbent articles such as adult incontinent articles, children's training pants, feminine hygiene articles, and the like. An exemplary absorbent article is disclosed in U.S. Pat. No. 5,853,402, issued Dec. 29, 1998 to Faulks et al., the entirety of which is incorporated herein by reference where not contradictory.

A continuous web of articles, such as disposable diapers, may be constructed, severed and separated into discrete units on a manufacturing line, such as a diaper machine. The discrete articles may then be presented to an apparatus, such as a folder, to be manipulated and prepared for packaging. An exemplary method and apparatus for making an absorbent article is disclosed in U.S. Pat. No. 5,743,994, issued Apr. 28, 1998 to Roessler et al., the entirety of which is incorporated herein by reference where not contradictory.

Figure 1:
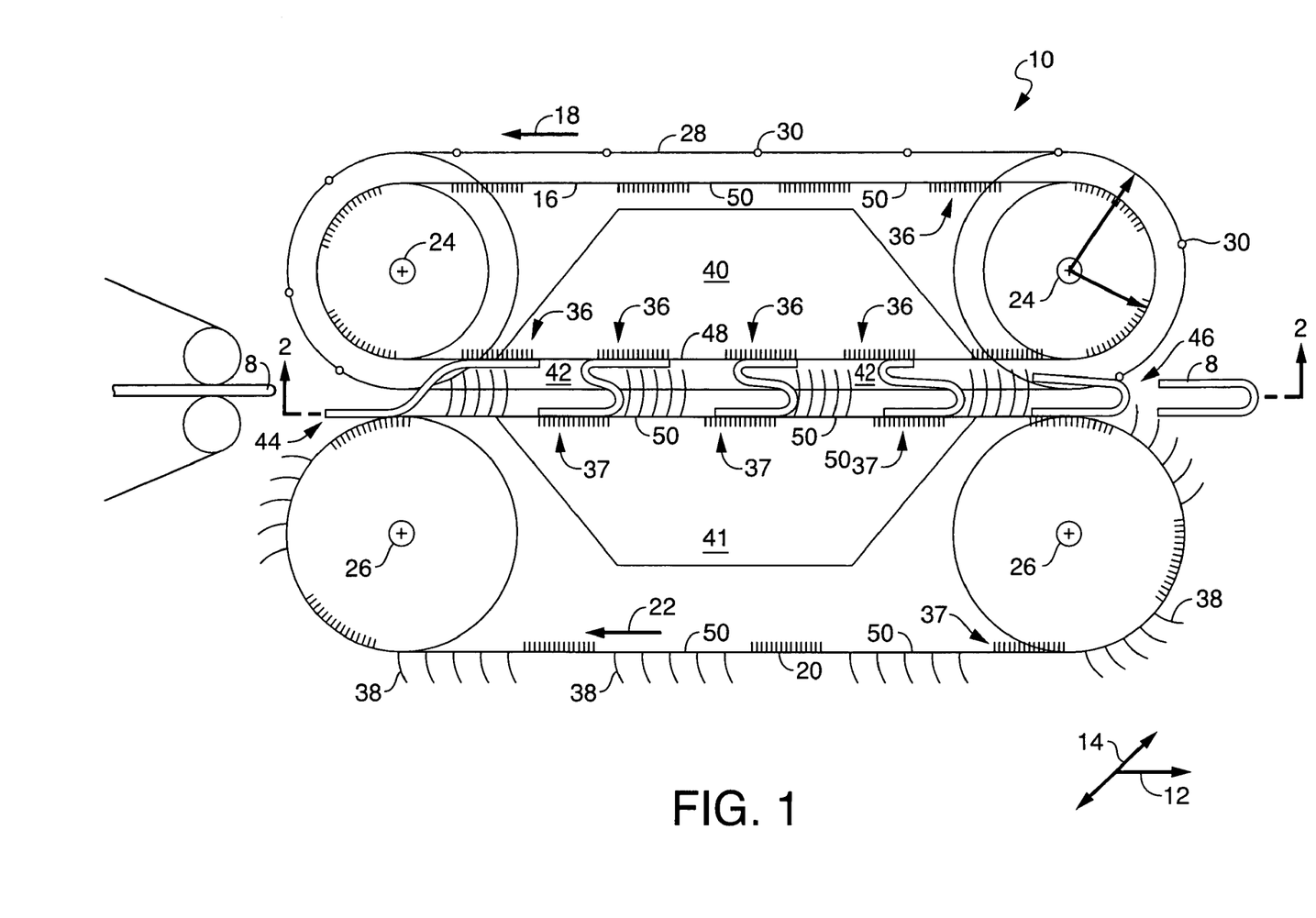
FIG. 1 representatively illustrates a schematic side elevation view of an exemplary method and apparatus of one embodiment of the present invention.

FIG. 1 is a schematic side view of a representative article 8 moving through a representative folder 10 in a machine direction 12. Perpendicular to the machine direction 12 is a cross-machine direction 14. The folder 10 includes a first conveyor 16 moving in a direction indicated by an arrow 18 and a second conveyor 20 moving in a direction indicated by an arrow 22. The first conveyor 16 and the second conveyor 20 are oriented in facing relation and define a folding zone 42 therebetween. The folding zone 42 has a folding zone entrance 44 and a folding zone exit 46.

The first conveyor 16 and the second conveyor 20 further include a plurality of vacuum areas 36 and 37 respectively and vacuum boxes 40 and 41 respectively. Additionally, the first conveyor 16 and the second conveyor 20 further include a plurality of vacuum impermeable areas 48 and 50 respectively. A vacuum source (not illustrated) creates a vacuum in the vacuum boxes 40 and 41. When vacuum areas 36 and 37 pass over the vacuum boxes 40 and 41, air is drawn through the conveyors 16 and 20 at the vacuum areas 36 and 37 respectively. When the vacuum impermeable areas 48 and 50 pass over the vacuum boxes 40 and 41, a reduced amount of air passes through the conveyors 16 and 20. In various embodiments, the vacuum areas 36 and 37 may be created by any suitable method, such as, for example, a plurality of slits, apertures, or the like, created in the conveyors 16 and 20. In various embodiments, the vacuum impermeable areas 48 and 50 may allow less air to pass relative to the vacuum areas 36 and 37 or may be adapted to completely block air from passing through the conveyors 16 and 20 in these areas.

In some embodiments, such as illustrated in FIG. 1, the second conveyor may optionally include a plurality of profiles 38 adapted to position the article 8 closer to the first conveyor 16 in the folding zone 42. Generally, the profiles 38 are located along the second conveyor 20 in the vacuum impermeable areas 50.

The folder 10 further includes a plurality of folding guides 30. The folding guides 30, as illustrated, are generally oriented in the cross-machine direction 12 and are operatively attached to one or more guide transporters 28. The guide transporters 28 may include one or more chains, belts, conveyors, and the like, and combinations thereof. The guide transporters 28 are adapted to move the folding guides 30 in the machine direction 12 through the folding zone 42 in contact with the articles 8. The guide transporters 28 may also move the folding guides 30 in various other directions outside the folding zone 42 as long as the folding guides 30 are returned to the folding zone entrance 44 and subsequently moved through the folding zone 42.

Figure 2:
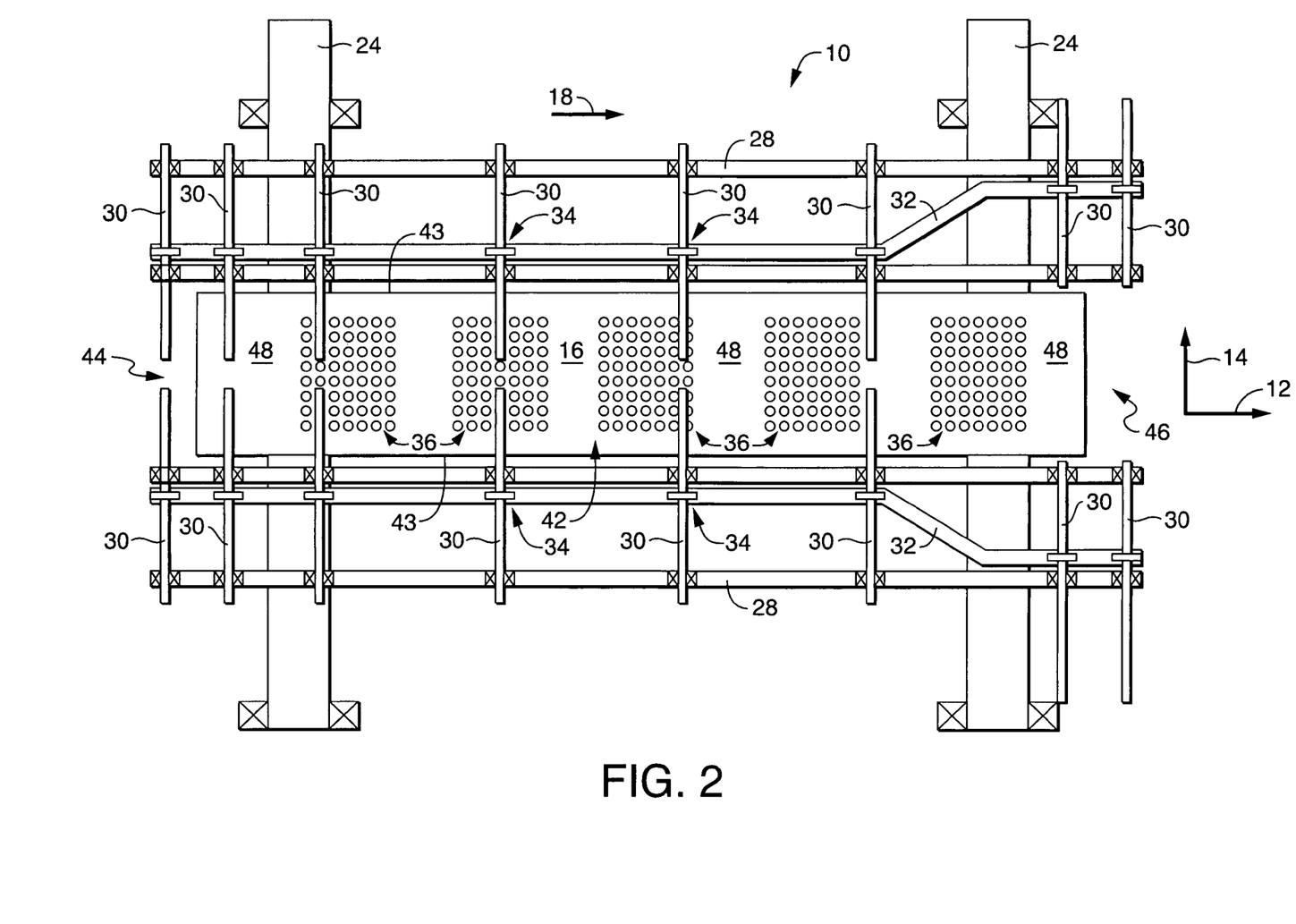
FIG. 2 representatively illustrates a view of the apparatus of FIG. 1 taken along the line 2-2.

FIG. 2 representatively illustrates the view taken along the line 2-2 of FIG. 1 with the article 8 removed for clarity. The first conveyor 16 of the folder 10 can be seen with vacuum areas 36 representatively illustrated by a plurality of circles. The first conveyor 16 moves in the direction 18, which in the folding zone 42 is the same as the machine direction 12. The folding zone 42 has longitudinal side edges 43 parallel to the machine direction 12. The guide transporters 28 are illustrated as two chains located along the sides of the first conveyor 16 and along the longitudinal sides 43 of the folding zone 42. The folding guides 30, as illustrated, are generally oriented in the cross-machine direction 14 and include cam followers 34 that are adapted to engage cam tracks 32. The cam tracks 32 are generally located on the sides of the first conveyor 16 and are adapted such that the folding guides 30 extend into the folding zone 42 near the folding zone entrance 44, move through the folding zone 42 and move out of the folding zone 42 near the folding zone exit 46.

The conveyors 16 and 20 may be the length of several unfolded articles. For example, in the illustrated embodiments, the conveyors 16 and 20 are about six articles long. However, the conveyors may be any suitable length. The vacuum areas 36 of the first conveyor 16, as illustrated, are adapted so as to correspond to approximately the leading half of each article 8 to be folded as it travels through the folder 10. Likewise, the second conveyor 20 includes vacuum areas 37 (visible in FIGS. 1, 3A-3E) adapted to correspond approximately to the trailing half of each article 8. When vacuum is applied to the vacuum box 40, the leading portion of the articles 8 are drawn, via vacuum, to the first conveyor 16 at the vacuum areas 36. In various embodiments, the addition of the profiles 38 may lift and/or guide the leading portions of the articles 8 into closer proximity to the first conveyor 16 to facilitate the vacuum adhesion therebetween. Likewise, when vacuum is applied to the vacuum box 41, the trailing portions of the articles 8 are drawn by vacuum to the second conveyor 20.

In various embodiments, the guide transporter 28 need only be located and oriented such that the folding guides 30, attached thereto, pass in contact with the articles 8 through the folding zone 42. For example, the guide transporter 28 may be a side lug belt that includes conveyors moving about shafts oriented in the direction perpendicular to the plane defined by the machine direction 12 and the cross-machine direction 14 as representatively illustrated in FIG. 2A.

Figure 2A:
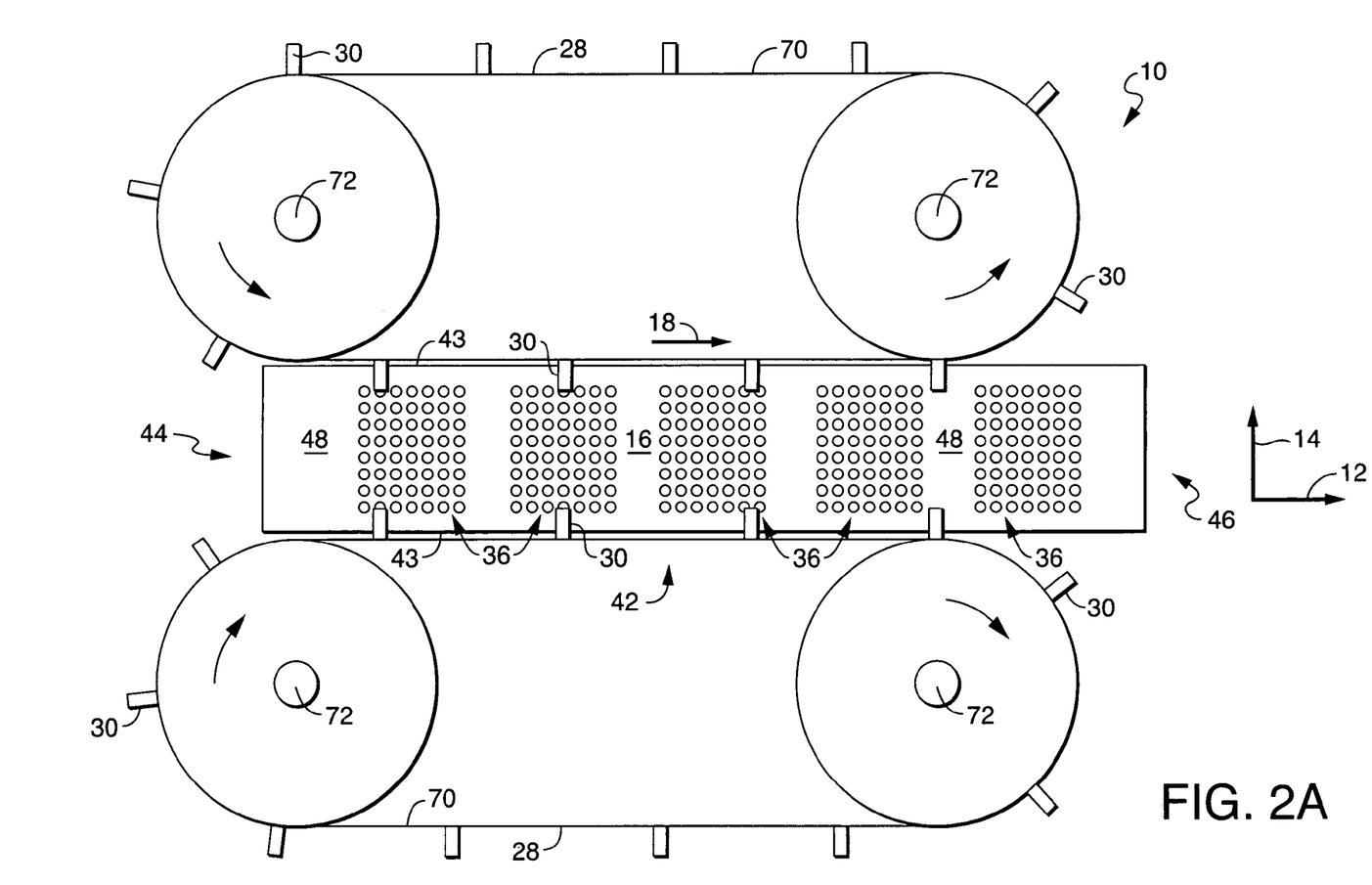
FIG. 2A representatively illustrates an alternative guide transporter.

FIG. 2A representatively illustrates an alternative guide transporter 28 suitable for moving a plurality of folding guides 30 attached thereto through the folding zone 42. Like FIG. 2, the first conveyor 16 of the folder 10 can be seen with vacuum areas 36 representatively illustrated by a plurality of circles. The first conveyor 16 moves in the direction 18, which in the folding zone 42 is the same as the machine direction 12. The guide transporter 28 is illustrated as two lugged chains located on the sides of the first conveyor 16. The folding guides 30 are generally oriented in the cross-machine direction 14 in the folding zone 42. The guide transporter 28 is adapted such that the folding guides 30, attached thereto, extend into the folding zone 42 near the folding zone entrance 44, move through the folding zone 42 and move out of the folding zone 42 near the folding zone exit 46.

Referring now to FIGS. 3A-3E, various steps in the folding process and various portions of the folding zone 42 are illustrated in greater detail. The article 8 has a first surface 58, a second surface 59, a leading edge 60, a trailing edge 61, a leading portion 64, a trailing portion 66 and a central portion 65 connecting the leading portion 64 and the trailing portion 66. The vacuum areas 36 of the first conveyor 16 include a leading edge 86 and a trailing edge 87. Likewise, the vacuum areas 37 of the second conveyor 20 include a leading edge 88 and a trailing edge 89.

In FIGS. 3A-3E, the first conveyor 16 is adapted to move in the machine direction 12 at a first conveyor velocity, $V_1$. The folding guide 30 is adapted to move in the machine direction 12 at a folding guide velocity, $V_G$. The second conveyor 20 is adapted to move in the machine direction 12 at a second conveyor velocity, $V_2$. The first conveyor velocity, $V_1$, is less than the second conveyor velocity, $V_2$. This difference in velocity is such that by the time the article 8 moves through the folding zone 42 of the folder 10, the leading edge 86 of the vacuum area 36 of the first conveyor 16 is approximately aligned with the trailing edge 89 of the vacuum area 37 of the second conveyor 20. As a result the article 8 will be folded. The folding guide velocity, $V_G$, is the same as the second conveyor velocity, $V_2$. As such, the relative position, in the machine direction 12, of the folding guide 30 and the second conveyor 20 remains the same throughout the folding zone 42, thereby providing a point about which the article 8 may fold. If so desired, the various velocities may be adapted such half, more than half, or less than half the article 8 is folded over onto itself.

Figure 3A:
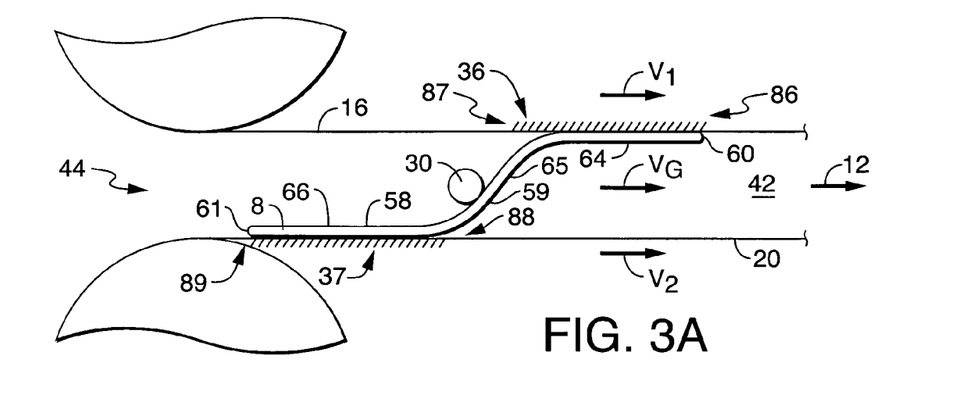
FIGS. 3A-3E representatively illustrate a schematic side elevation view of various stages and portions of an exemplary method and apparatus of one embodiment of the present invention as an article is folded.

In FIG. 3A, the article 8 enters the folding zone 42 at the folding zone entrance 44 and the first surface 58 of the leading portion 64 of the article 8 is drawn to the vacuum area 36 of the first conveyor 16 while the second surface 59 of the trailing portion 66 of the article 8 is drawn, via vacuum, to the vacuum area 37 of the second conveyor 20. As illustrated, the leading edge 60 of the article 8 may be generally aligned with the leading edge 86 of the vacuum area 36 of the first conveyor 16. Also, as illustrated, the trailing edge 61 of the article 8 may be generally aligned with the trailing edge 89 of the vacuum area 37 of the second conveyor 20.

Figure 3B:
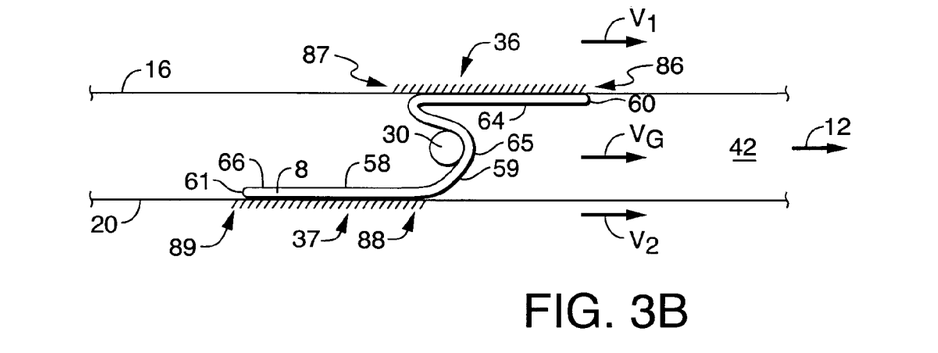
Figure 3C:
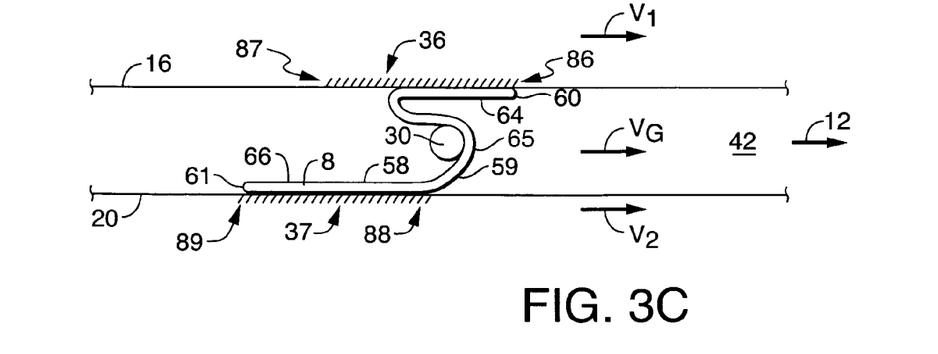
Figure 3D:
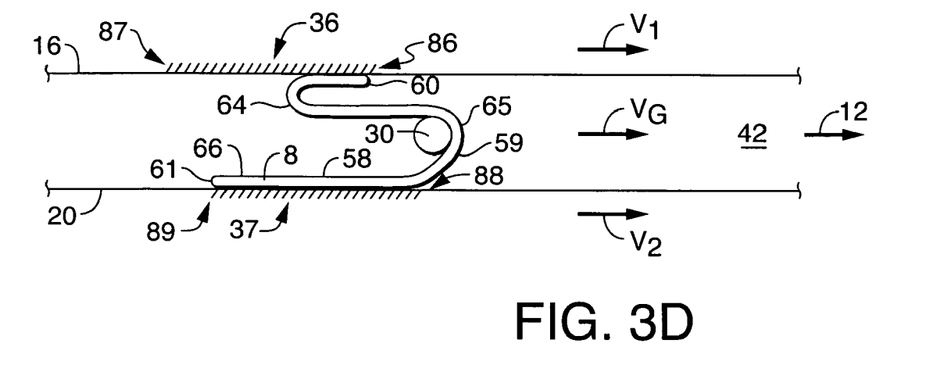
Figure 3E:
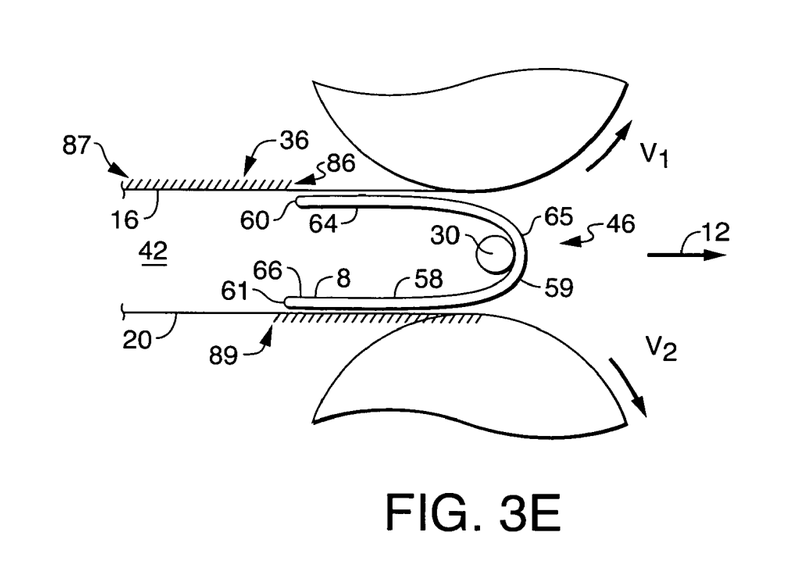

In FIGS. 3B-D, the article 8 continues to move though the folding zone 42 with the folding guides 30 contacting the first surface 58 of the central portions 65 of the articles 8. The leading portion 64 of the article 8, being drawn by vacuum to the slower moving first conveyor 16, begins to move backwards relative to the trailing portion 66 of the article 8, being drawn by vacuum to the faster moving second conveyor 20 and relative to the central portion 65 of the article 8 being contacted by the folding guide 30. As this happens, the first surface 58 of the leading portion 64 of the article 8 is peeled off the first conveyor 16 as illustrated in FIGS. 3B-D. As the article 8 nears the folding zone exit 46, the article 8 is completely folded over onto itself. The folded article 8 exits the folding zone 42 for subsequent processing, packaging, or the like.

In various embodiments, the folding guides 30 move out of the folding zone 42 via the cam tracks 32 and cam followers 34 as illustrated in FIG. 2. In other embodiments, the folding guides 30 move out of the folding zone 42 via a lugged belt as illustrated in FIG. 2A. In other embodiments, any suitable guide transporter 28 may be used to move the folding guides 30 out of the folding zone 42.

In various embodiments, the folding guide velocity, $V_G$, is preferably the same as the second conveyor velocity, $V_2$. This can be accomplished in various ways as is known to those skilled in the art. For example, the guide transporter 28, to which the folding guides 30 are attached, may be independently driven to achieve the desired velocity match. Alternately, the guide transporter 28 may be driven on the same shafts as the first conveyor 16 with appropriate gear ratios such that the folding guide velocity, $V_G$, matches the second conveyor velocity, $V_2$. Alternately, the guide transporter 28 may be driven on the same shafts as the second conveyor 20 with appropriate gear ratios such that the folding guide velocity, $V_G$, matches the second conveyor velocity, $V_2$.

In various embodiments, the folding guides 30 may pass through the folding zone 42 closer to the first conveyor 16, closer to the second conveyor 20, or equally distant from each. The folding guides 30 may be any suitable length, width and shape depending upon the characteristics of the product 8 being folded. For example, the folding guides 30 may have a cylindrical shape or may have a blade shape. The folding guides 30 may be manufactured from any suitable materials, such as, for example, metal, carbon fiber, or plastic. The folding guides 30 may include any suitable coatings, such as, for example, TEFLON®.

The illustrated examples include pairs of folding guides 30 extending into the folding zone 42 from each side. However, a single folding guide 30 extending into the folding zone 42 from one side may be adapted to provide suitable folding.

The first conveyor 16, the second conveyor 20 and/or the guide transporter 28 may be timing belts made of any suitable materials, such as, for example, polyurethane, neoprene, nylon, PVC or rubber and may be reinforced with steel, KEVLAR®, and the like. The first vacuum zones 36 and/or the second vacuum zones 37 may be created by any suitable means, such as, for example, by perforating a timing belt at the desired locations. The profiles 38 may be separately attached to the second conveyor 20 via welds, bolts or other suitable means. The profiles 38 may also be integrally formed with the conveyor. The profiles 38 may be made of polyurethane or other suitable material. Suitable timing belts are available from Gates Mectrol Corporation having offices at 9 Northwestern Drive, Salem, N.H., USA.

In various embodiments, the first conveyor velocity, $V_1$, may include any suitable range depending on the product being folded. In some embodiments, the first conveyor velocity, $V_1$, may range from 10 feet per minute to 2475 feet per minute.

In various embodiments, the second conveyor velocity, $V_2$, may include any suitable range depending on the product being folded. In some embodiments, the second conveyor velocity, $V_2$, may range from 10.1 feet per minute to 2500 feet per minute.

In various embodiments, the folding guide velocity, $V_G$, may include any suitable range depending on the product being folded. In some embodiments, the folding guide velocity, $V_G$, may range from 10.1 feet per minute to 2500 feet per minute.

In various embodiments, the ratio of the first conveyor velocity, $V_1$, to the second conveyor velocity, $V_2$, may include any suitable range depending on the product being folded. In some embodiments, the ratio of the first conveyor velocity, $V_1$, to the second conveyor velocity, $V_2$, may range from 0.5 to 1 up to 0.99 to 1. In various embodiments, the ratio may be less than 0.9 to 1, less than 0.8 to 1, less than 0.7 to 1, or less than 0.6 to 1.

The folders described herein are suitable for folding various articles. A method for folding articles includes supplying an article 8 to be folded. The article 8 has a first surface 58 and a second surface 59 opposite the first surface 58. The article 8 has a leading portion 64, a trailing portion 66 and a central portion 65 connecting the leading portion 64 and the trailing portion 66.

The method includes engaging the first surface 58 of the leading portion 64 of the article 8 with a first conveyor 16. The method includes moving the first conveyor 16 in a machine direction 12 at a first conveyor velocity, $V_1$. Also, the method includes engaging the second surface 59 of the trailing portion 66 of the article 8 with a second conveyor 20. The second conveyor 20 is moved in the machine direction 12 at a second conveyor velocity, $V_2$. The second conveyor velocity, $V_2$, is greater than the first conveyor velocity, $V_1$. As used herein, the terms "engage" or "engaging" means to attract, draw and/or hold such as, for example, by vacuum.

The method also includes contacting the first surface 58 of the article 8 with at least one folding guide 30 and moving the at least one folding guide 30 in the machine direction 12 at a folding guide velocity, $V_G$. The folding guide velocity, $V_G$, is the same as the second conveyor velocity $V_2$. In various embodiments, the at least one folding guide 30 may contact the leading portion 64, the trailing portion 66, or the central portion 65 of the article 8.

The method of folding may further include peeling the first surface 58 of the leading portion 64 of the article 8 from the first conveyor 16 as the article 8 moves between the slower first conveyor 16 and the faster second conveyor 20 thereby folding the article 8 about the folding guide 30 such that the first surface 58 of the leading portion 64 is in facing relation with the first surface 58 of the trailing portion 66 of the product 8. In some embodiments, the leading edge 60 may be generally aligned with the trailing edge 61 such that the article 8 is folded in half.

In various embodiments, the method can include moving the folding guides 30 into the folding zone 42 near the folding zone entrance 44 and removing the folding guides 30 from the folding zone 42 near the folding zone exit 46. The folding guides 30 may be moved by one or more suitable folding guide transporters 28.

In some embodiments, the method includes moving the folding guides 30 via a chain along cam tracks 32 using cam followers 34 as illustrated in FIG. 2. As the folding guides 30 approach the folding zone entrance 44, the cam followers 34 associated with the folding guides 30 move along the cam tracks 32 causing the folding guides 30 to move into the folding zone 44. The guide transporter 28 moves the folding guides 30 in the machine direction 12 through the folding zone 42. As the folding guides 30 approach the folding zone exit 46, the cam followers 34 associated with the folding guides 30 move along the cam tracks 32 moving the folding guides 30 out of the folding zone 44. The guide transporters 28 continue to move the folding guides 30 in a direction opposite the machine direction 12 to return the folding guides 30 to the folding zone entrance 44 wherein the process is repeated.

In other embodiments, the method includes moving the folding guides 30 using a pair of lugged belts 70 as the guide transporter 28 as illustrated in FIG. 2A. The lugged belts 70 run about shafts 72 oriented orthogonally to the plane defined by the machine direction 12 and the cross-machine direction 14. The folding guides 30 are orthogonally attached to the lugged belt 70 such that as the belts 70 rotate about the shafts 72 the folding guides 30 approach the folding zone entrance 44 and move into the folding zone 44. The lugged belts 70 move the folding guides 30 in the machine direction 12 through the folding zone 42. As the folding guides 30 approach the folding zone exit 46 the belts 70 rotate about the shafts 72 moving the folding guides 30 out of the folding zone 44. The belts 70 continue to move the folding guides 30 in a direction opposite the machine direction 12 to return the folding guides 30 to the folding zone entrance 44 wherein the process is repeated.

In some embodiments, the second conveyor 20 includes profiles 38 located in the vacuum impermeable areas 50 as illustrated in FIG. 1. The method of folding a product using this apparatus is similar to that described above but with the additional step of guiding the leading portion 64 of the article 8 into closer proximity to the vacuum areas 36 of the first conveyor 16 by lifting the leading portion 64 of the article 8 with the profiles 38 as illustrated in FIG. 1.

In various embodiments, the method may similarly be utilized to fold an article such that the second surface 59 of the leading portion 64 is in facing relation with the second surface 59 of the trailing portion 66 by reversing the orientation of the article 8 before entering the folder 10. As such, the second surface 59 would be drawn, via vacuum, to the first conveyor 16, the first surface 58 would be drawn, via vacuum, to the second conveyor 20 and the second surface 58 would be in contact with the folding guide 30.

Figure 4:
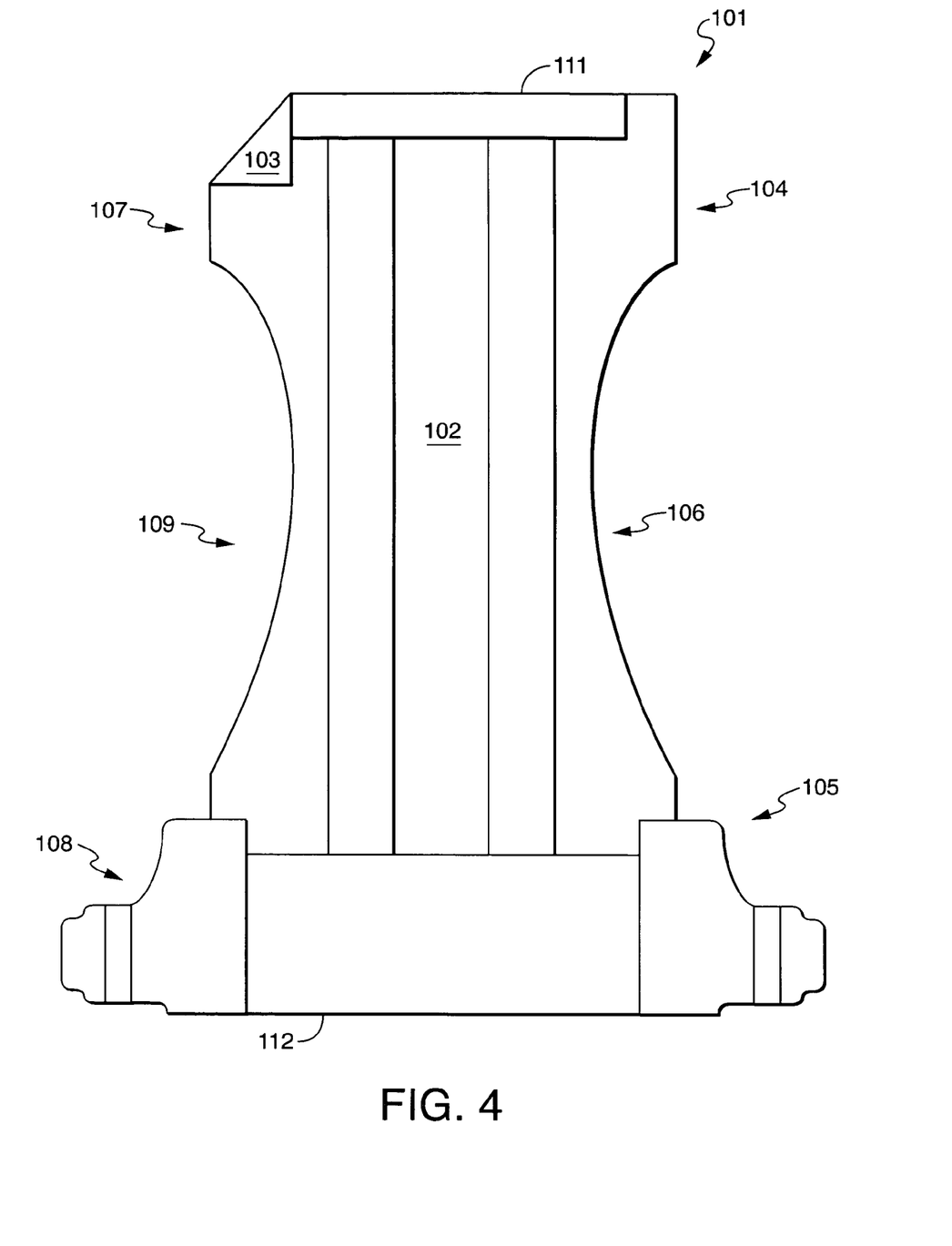
FIG. 4 representatively illustrates an exemplary diaper suitable for folding using the method and apparatus of the present invention.

The folders described herein are also suitable for folding disposable diapers. FIG. 4 representatively illustrates an exemplary diaper shown generally at 101. The diaper 101 has a body side 102 and a garment side 103 opposite the bodyside 102. Typically, the body side 102 comprises a liner and the garment side 103 comprises an outer cover. The diaper 101 has a front portion 104, a rear portion 105 and a crotch portion 106 connecting the front portion 104 and the rear portion 105. In use, the front portion 104 is generally oriented in the front of the baby, the rear portion 105 is generally oriented to the rear of the baby and the crotch portion 106 is generally oriented between the legs of the baby. The diaper 101 also has a leading portion 107, a trailing portion 108 and a central portion 109 connecting the leading portion 107 and the trailing portion 108. The leading portion 107 also has a leading edge 111 and the trailing portion 108 has a trailing edge 112.

In various embodiments, the front portion 104 may be the leading portion 107 and the rear portion 105 may be the trailing portion 108. In various embodiments, the front portion 104 may be the trailing portion 108 and the rear portion 105 may be the leading portion 107.

A method for folding a diaper includes supplying a diaper 101 as is known in the art. As is known in the art, the diaper 101 may include one or more additional folds in the machine direction before being introduced to the folder 10. The method includes engaging the garment side 103 of the trailing portion 108, via vacuum, to a perforated portion 37 of a second conveyor 20 and then moving the second conveyor 20 in the machine direction 12 at a second conveyor velocity, $V_2$.

The method includes moving the leading portion 107 towards the perforated portion 36 of the first conveyor 16. The method may also include lifting the leading portion 107 of the diaper 101, via profiles 38 attached to the second conveyor 20, into closer proximity to the perforated portion 36 of the first conveyor 16. The first conveyor 16 is moved in a machine direction 12 at a first conveyor velocity, $V_1$. The first conveyor velocity, $V_1$, is less than the second conveyor velocity, $V_2$.

In various embodiments, the method may further include engaging the body side 102 of the leading portion 107, via vacuum, to the perforated portion 36 of the first conveyor 16, contacting the body side 102 of the central portion 109 with a pair of folding guides 30. The folding guides 30, are moved in the machine direction 12 at the second conveyor velocity, $V_2$.

The method may further include peeling the body side 102 of the leading portion 107 of the diaper 101 from the first conveyor 16 as the diaper 101 moves between the slower first conveyor 16 and the faster second conveyor 20 thereby folding the diaper 101 about the pair of folding guides 30 such that the body side 102 of the leading portion 107 is in facing relation with the body side 102 of the trailing portion 108.

In various embodiments, the method may include aligning the leading edge 111 of the leading portion 107 with the trailing edge 112 of the trailing portion 108.

In various embodiments, the method may include moving the first and second conveyors such that the ratio of the first conveyor velocity to the second conveyor velocity is less than 0.8 to 1.

In various embodiments, the method may include engaging the body side 102 of the trailing portion 108, via vacuum, to a perforated portion 37 of a second conveyor 20 and then moving the second conveyor 20 in the machine direction 12 at a second conveyor velocity, $V_2$.

The method may include moving the leading portion 107 towards the perforated portion 36 of the first conveyor 16. The method may also include lifting the leading portion 107 of the diaper 101, via profiles 38 attached to the second conveyor 20, into closer proximity to the perforated portion 36 of the first conveyor 16. The first conveyor 16 is moved in a machine direction 12 at a first conveyor velocity, $V_1$. The first conveyor velocity, $V_1$, is less than the second conveyor velocity, $V_2$.

In various embodiments, the method may further include engaging the garment side 103 of the leading portion 107, via vacuum, to the perforated portion 36 of the first conveyor 16, contacting the garment side 103 of the central portion 109 with a pair of folding guides 30. The folding guides 30 are moved in the machine direction 12 at the second conveyor velocity, $V_2$.

The method may further include peeling the garment side 103 of the leading portion 107 of the diaper 101 from the first conveyor 16 as the diaper 101 moves between the slower first conveyor 16 and the faster second conveyor 20 thereby folding the diaper 101 about the pair of folding guides 30. The folded diaper 101 has the garment side 103 of the leading portion 107 in facing relation with the garment side 103 of the trailing portion 108.

While the invention has been described in detail with respect to specific embodiments thereof, it will be appreciated that those skilled in the art, upon attaining an understanding of the foregoing will readily conceive of alterations to, variation of and equivalents to these embodiments. Accordingly, the scope of the present invention should be assessed as that of the appended claims and any equivalents thereto.

The invention claimed is:

1. A method for folding an article comprising:
   supplying an article having a first surface and a second surface opposite the first surface, the article having a leading portion, a trailing portion and a central portion connecting the leading portion and the trailing portion;
   engaging the first surface of the leading portion of the article with a first conveyor;
   moving the first conveyor in a machine direction at a first conveyor velocity;
   engaging the second surface of the trailing portion of the article with a second conveyor;
   moving the second conveyor in the machine direction at a second conveyor velocity, the second conveyor velocity being greater than the first conveyor velocity;
   contacting the first surface of the article with at least one folding guide;
   moving the at least one folding guide in the machine direction at the second conveyor velocity; and
   folding the article about the at least one folding guide such that the first surface of the leading portion is in facing relation with the first surface of the trailing portion.

2. The method of claim 1 further comprising moving the first conveyor at the first conveyor velocity and moving the second conveyor at the second conveyor velocity wherein the ratio of the first conveyor velocity to the second conveyor velocity is less than 0.8 to 1.

3. The method of claim 1 wherein the folding step further includes peeling the first surface of the leading portion of the article from the first conveyor as the article moves between the first conveyor and the second conveyor.

4. The method of claim 1 wherein the method further includes applying vacuum to vacuum areas in the first conveyor and vacuum areas in the second conveyor and engaging the first surface of the leading portion of the articles with the vacuum areas of the first conveyor and engaging the second surface of the trailing portion of the articles with the vacuum areas of the second conveyor.

5. The method of claim 4 wherein the method further includes moving the leading portion of the article towards the vacuum areas of the first conveyor.

6. The method of claim 5 wherein the method further includes lifting the leading portion of the article with profiles attached to the second conveyor.

7. A method for folding a diaper comprising:
   supplying a diaper having a body side, a garment side opposite the body side, a leading portion, a trailing portion, and a central portion connecting the leading portion and the trailing portion;
   engaging the garment side of the trailing portion, via vacuum, to a perforated portion of a second conveyor;

moving the second conveyor in a machine direction at a second conveyor velocity;

moving the leading portion of the diaper towards a perforated portion of a first conveyor;

engaging the body side of the leading portion, via vacuum, to the perforated portion of the first conveyor;

moving the first conveyor in the machine direction at a first conveyor velocity, the first conveyor velocity being less than the second conveyor velocity;

contacting the body side of the diaper with a pair of folding guides;

moving the folding guides in the machine direction at the second conveyor velocity;

moving the diaper through a folding zone defined by the first conveyor and the second conveyor;

peeling the body side of the leading portion of the diaper from the first conveyor as the diaper moves through the folding zone, thereby folding the diaper about the pair of folding guides, such that the body side of the leading portion is in facing relation with the body side of the trailing portion.

8. The method of claim 7 further comprising lifting the leading portion of the diaper towards the perforated portion of the first conveyor with profiles attached to the second conveyor.

9. The method of claim 7 further comprising aligning a leading edge of the leading portion with a trailing edge of the trailing portion.

10. The method of claim 7 further comprising moving the first and second conveyors such that the ratio of the first conveyor velocity to the second conveyor velocity is less than 0.8 to 1.

* * * * *